United States Patent [19]

Chu et al.

[11] Patent Number: 4,709,067

[45] Date of Patent: Nov. 24, 1987

[54] METHOD FOR PREPARING METHACRYLOXY AND ACRYLOXY CONTAINING ORGANOSILANES AND ORGANOSILICONES

[75] Inventors: Nan S. Chu, Hartsdale; Bernard Kanner, West Nyack, both of N.Y.

[73] Assignee: Union Carbide Corporation, Danbury, Conn.

[21] Appl. No.: 865,009

[22] Filed: May 20, 1986

[51] Int. Cl.$^4$ .............................. C07F 7/18; C07F 7/08
[52] U.S. Cl. .................................... 556/440; 556/437; 556/479
[58] Field of Search ................................ 556/440, 437

[56] References Cited

U.S. PATENT DOCUMENTS

| | | | |
|---|---|---|---|
| 3,258,477 | 6/1966 | Plueddemann et al. | 556/440 |
| 4,276,426 | 6/1981 | Lindner et al. | 556/479 |
| 4,304,920 | 12/1981 | Arai et al. | 556/440 |
| 4,558,111 | 12/1985 | Tolentino | 556/440 X |

Primary Examiner—Paul F. Shaver
Attorney, Agent, or Firm—P. W. Luezzi

[57] ABSTRACT

This invention relates to an improved process for preparing, purifying and/or storing methacryloxy or acryloxy containing organosilicon compounds without the undesirable polymerization normally associated with the methacrylate bonds. In an alternative embodiment, the process is even further improved with the addition of certain stabilizers, and in particular diketone or ketoester stabilizers.

71 Claims, No Drawings

METHOD FOR PREPARING METHACRYLOXY AND ACRYLOXY CONTAINING ORGANOSILANES AND ORGANOSILICONES

BACKGROUND OF THE INVENTION

1. Field of the Invention

This invention relates generally to a novel method for improving yields in hydrosilation reactions. More particularly, this invention relates to an improved method for preparing methacryloxy and acryloxy containing organosilanes and organosilicones under certain conditions without the unwanted polymerization, i.e., gellation, generally associated with the reactions involving these compounds. The process is further improved when a stabilizer is used to obviate some of the specific conditions required to avoid gellation.

2. Prior Art

The hydrosilation reaction, the addition of silicon hydrides to unsaturated compounds, is the most common method for the preparation of organosilicon compounds with functional groups in the organic position of the molecules. There are numerous literatures which teach how to carry out hydrosilation reactions with various unsaturated compounds such as alkenes, unsaturated ethers, amines, etc. 1 C. Earborn and R. W. Bott, Organometallic compounds of the Group IV Elements (1968).

These methods, however, are not suitable for the preparation of compounds containing methacryloxy, $CH_2=C(CH_3)COO-$, and/or acryloxy, $CH_2=CHCOO-$, functional groups. This is because, unlike the other organosilicon compounds, methacryloxy and acryloxy containing organosilicon compounds can polymerize easily during preparation and/or purification through reaction of the methacrylate double bonds. Such polymerization not only results in wasted products, but also renders clean up very difficult, if not impossible, because of the gelled product inside.

U.S. Pat. No. 3,258,477 to Plueddemann et al. teaches the preparation of a stable γ-methacryloxypropyltrimethoxysilane by simultaneously charging both trimethoxysilane and allyl methacrylate into a toluene solution containing 2,5 ditertiarylbutylhydroquinone, additional trimsthoxysilane and a solution of chloroplatinic acid all at 105° C. The use of large amounts of toluene as a solvent, however, makes this process rather expensive and economically unattractive.

In U.S. Pat. No. 4,276,426 to Lindner et al., γ-methacryloxypropyltrichlorosilane was again prepared without gellation when trichlorosilane, allyl methacrylate and platinum catalyst were continuously introduced into a pipe-shaped reactor and circulated in the reactor while the reaction mixture was continuously being removed from the reactor. In this reference, the improvement of the process comprised continuously circulating the reaction mixture in the reactor at at least 1000 centimeters per minute. The contents of the reactor will gel when the contents are not continually circulated, i.e., this process cannot be carried out as a batch process.

Thus, there is no teaching in the prior art of a process to halt the undesirable polymerization caused by methacryloxy and acryloxy containing organosilicon compounds which process does not require either the use of large amounts of solvents or the continuous circulation of the reaction product mixture. There is a need in the art for a more economic and more expedient process for preparing these compounds. Further, there is a need to insure undesirable polymerization does not occur during preparation, purification or storage of the compounds.

OBJECTIVES

It is thus an object of this invention to provide a more economic and more expedient process for preparing methacryloxy and acryloxy containing organosilicon compounds.

It is a further object of this invention to insure that undesirable polymerization does not occur during the preparation, purification or storage of these compounds.

It is an even further object of this invention to provide a process for treating the products of this reaction such that undesirable polymerization is avoided.

Another object of the invention is to provide an even further improvement by providing stabilizers which may obviate the special post treatment step of this invention used to reduce undesirable polymerization.

Yet another object of this invention is to provide such a process which can be economically and efficiently run as either a batch or a continuous process.

Other objects and advantages of the invention will become apparent as the description thereof proceeds.

BRIEF SUMMARY OF THE INVENTION

In satisfaction of the foregoing objects, this invention relates to a novel process for eliminating undesirable polymerization associated with the acrylate double bonds found in methacryloxy or acryloxy containing organosilicon compounds. The process eliminates this unwanted polymerization by (1) combining the contents of a first reservoir containing a methacryloxy or acryloxy containing compound and an inhibitor or inhibitors with a second reservoir containing alkoxy silane or an SiH containing silicone and a platinum catalyst under appropriate conditions, (2) post-treating the reaction product with alcohol and/or a heat treatment, and (3) vacuum distilling the post-treated product.

In an alternative embodiment of the invention, stabilizers are added to the first reservoir containing the methacryloxy or acryloxy starting reactant and inhibitor or inhibitors. The use of these stabilizers further reduces undesirable polymerization and, when used, obviates the post-treatment step.

The present invention may be practiced as a batch process as well as a continuous process.

DETAILED DESCRIPTION OF THE INVENTION

In accordance with the present invention, there is provided a novel process for eliminating undesirable polymerization or gellation which occurs in methacryloxy or acryloxy containing organosilicon compounds. More specifically it has been found that acryloxypropyltrialkoxysilanes such as γ-methacryloxypropyltrimethoxysilane or γ-acryloxypropyltrimethoxysilane can be prepared and purified without polymerization problems when the reactants, trialkoxysilane or SiH containing silicone, allyl methacrylate or allyl acrylate and the platinum catalyst, are brought together.

The process of the invention comprises the steps of:

(1) charging a first reservoir with a methacryloxy or acryloxy functional containing compound and an inhibitor or inhibitors;

(2) charging a second reservoir with an alkoxysilane or an SiH containing silicone and a platinum-containing hydrosilation compound;

(3) combining the contents of the two reservoirs in a reactor vessel at the appropriate temperature;

(4) post treating the crude reaction product with alcohol or post heating the products at the appropriate temperature and for the appropriate time; and (5) vacuum distilling the post-treated products in the presence of inhibitors and under reduced pressure.

The present invention may be further improved by addition of stabilizers to the first reservoir containing methacryloxy and acryloxy functional compounds.

The addition of these stabilizers obviates the post-treatment step; the use of these stabilizers also makes the system less sensitive to polymerization and thus reduces the quantity of excess methacryloxy and acryloxy functional compounds which are used when no stabilizers are present to react with unreacted Si-H compounds or unreacted alkoxysilanes and thus halt their polymerization.

The process of this invention can be carried out as a batch or as a continuous process. This has no consequences with regard to the parameters of the invention except as to how it affects the order of combining the reactants.

For example, when the preparation of methacryloxy containing organosilicon compound is carried out by a continuous process, the platinum catalyst should be mixed together with the alkoxysilane before combining with the methacrylate or acrylate compound and inhibitor. Thus, the platinum catalyst can be either dissolved in alkoxysilane and the mixture dropped into the methacrylate inhibitor mixture at reaction temperature, as in the continuous process, or the platinum catalyst can be added incrementally to the hydrosilation mixture, as when the preparation is carried out batch-wise. In any case, one should avoid heating the platinum catalyst with the methacrylate-inhibitor mixture to reaction temperature and then dropping in the silane to the platinum-methacrylate inhibitor mixture, because gellation of the reaction mixture often results when this mode of addition is used. This latter scenario will not occur if the reservoirs are kept separate as indicated by the process steps.

It should be noted that it is important, in the continuous reaction, to keep the reaction mixture moving all the time in order to preclude undesired polymerization from occurring. The continuous unit should also be washed at the end of each preparation with an inert solvent such as toluene.

The silanes which can be used in this process may be represented by the general formula:

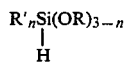

wherein R and R' are lower alkyl moieties containing 1 to 20 carbons or more preferably with 1 to 4 carbon atoms and n eguals 0 to 1.

The SiH containing silicone of this invention is a polysiloxane polymer with the general formula:

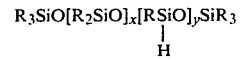

where R is a lower alkyl group having 1 to 8 carbons or an aryl group having 6 to 10 carbons, methyl is the preferred R group, x can range from 0 to 100 and y can range from 1 to 30.

Reactants containing methacryloxy or acryloxy functional groups may be represented by the general formula:

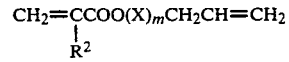

wherein $R^2$ is hydrogen a lower alkyl group having 2 to 8 carbons or an aryl group having 6 to 10 carbons, X is $CH_2CH_2O$ or a $CH_2$ group or a combination of the two groups, and m equals 0 to 10 or, preferably, 0 to 5.

The amount of methacryloxy containing compound, when no stablizer is used, should always be used in 2 to 10% molar excess over the stochiometric amount needed to react with the silane or polysiloxane polymer or, preferably, in 3-5% molar excess. As discussed above, the excess use of methacrylate or acrylate components over the stoichiometric require amount will prevent the presence of significant amounts of unreacted alkoxysilanes or Si-H containing polysiloxanes in the crude reaction product.

Inhibitors are used during two stages of the present process: during the hydrosilation reaction and during the vacuum distillation of the post-treated product.

Inhibitors which may be used in either the hydrosilation or vacuu distillation steps of this process include phenolic inhibitors such as monomethyl ether of hyroquinone ("MMHQ") or Isonox# 129, aromatic amines such as diphenylendiamine, aromatic sulfur compounds such as phenothiazine ("PTZ") or combinations thereof. Although both these non-phenolic and phenolic inhibitors may be used during either step, it is preferred to use only phenolic inhibitors, e.g., MMHQ, Ionol or Isonox# 129 for the hydrosilation reaction step. A combination of both phenolic and non phenolic inhibitors is preferred during vacuum distillation. The concentration of the inhibitor used during hydrosilaton varies in the range of 0.2 to 5.0% by weight base on methacrylate or acrylate or, preferably, in the 10.5-2.0% range. For vacuum distillation, the concentration of non phenolic varies in the range of 200 to 10,000 ppm while the concentration of phenolic inhibitor varies from 500 to 15,000 ppm, based on the weight of product used.

The platinum-containing hydrosilation catalyst used in the invention may be chosen from the group of supported platinum-catalysts, such as platinum on γ-alumina or on charcoal, or from the group of homogeneous soluble platinum complexes such as chloroplatinic acid bis-(ethylene platinous)chloride, dichlorobis-(acetonitrile)platinum (II), cis-dichlorobis(triphenylphosphine)platinum (II), tetrakis(triphenylphosphine)-platinum (O) or other soluble platinum complexes well known in the art. The soluble Platinum complexes are normally in solution in solvents such as isopropanol, acetonitrile or 1,2-dimethoxyethane. The concentration of the platinum catalyst required depends on reaction temperature and time but is generally used in the range of 2 to 100 ppm and preferably 10 to 25 ppm, based on the total weight of the hydrosilane or Si-H containing silicone and allyl methacrylate.

To improve the distillation stability of the crude products in the reaction vessel, the reaction mixture has to be post-treated with a small amount of alcohol such as methanol and/or heated at about 120° C. for a period of time. Otherwise, other gellation may occur during the vacuum distillation step or during storage or the yield percent of final product may be signifiantly reduced. The exact reason why post-treatments improve the stability of crude product is not known. But comparison of gas chromatograms taken before or after the post-treatment showed that both treatments, alcohol addition or heating at about 120° C., remove the unreacted alkoxysilane or SiH containing silicone left in the mixture as well as small amounts of by-product.

The amount of alcohol required for the post-treatment depends upon the amount of unreacted alkoxysilane or SiH containing silicone left in the reaction mixture. Under normal conditions when the reaction mixture. Under normal conditions when the hydrosilation is carried out to completion, i.e., the alkoxysilane or Si—H containing silicone left unreacted is less than 1% by GC analysis, an addition of 1–3% of alcohol by weight based on weight of product made is enough; although an amount higher than 3% can also be used up until about 5%. Any alcohol ROH, where R is a 1 to 10 carbon atom alkyl group, can be used, but methanol is the most preferred.

Post-treatment requires heating the reaction mixture in the presence of inhibitors at 100°–140° C. for 5 to 40 minutes, or more preferably at 110°–130° C. for 20 to 30 minutes.

After the post treatment(s), crude methacryloxy and acryloxy containing organosilicon compounds can be distilled in the presence of the above defined inhibitors under reduced pressure.

According to the continuous process of the invention, the methacrylate/acrylate-inhibitor mixture of the first rservoir should be preheated to 85° to 100° C. or preferably at 90° to 100° C. The preheating of the methcrylate will make the temperature at the point where the reactants from the two reservoirs meet at 70° to 90° C., preferably 75° to 85° C. The oil bath temperature at which the reactor vessel is kept is best kept at 80° to 120° C. or preferably at 90° to 110° C.

When the reacion is carried out in batch, the first reservoir can be the reactor itself, the second reservoir an additional funnel. The reactants in the reactor are also preheated to 85°–100° C. or preferably at 90°–100° C. before the reactants in the funnel are dropped in. The preferred reaction temperature is at 80°–120° C. or, more preferably, at 90°–110° C. A reaction temperature lower than 180° C. can also be used, but the reaction takes longer time to run and the unreacted alkoxysilane remaining in the reaction will also be higher. The higher the amount of unreacted alkoxysilane remaining in the reaction mixture, the larger the chance the product will gel during distillation and storage if not post treated. Gellation duing hydrosilation may occur when the hydrosilation is carried out at reaction temperatures above 125° C.

For both the continuous or the batch process, both residence time of the reaction mixture and charging rate of reactants depend on the size of the reactor and the temperature of the oil bath used. It is not critial to use specific residence times and/or charging rates. For the continuous process, it is important that the charging rates have to be regulated in such a way that the contents of the reaction mixture, after passing through the continuous reactor, contain little or no unreacted alkoxysilane or Si—H containing silicone and that the mixture in the realtor be kept moving all the time.

In another aspect of the invention, the stability of methacryloxy and acryloxy containing organosilicon compound may be further improved when compounds such as diketone and ketoester are used together with the inhibitor in the first reaction reservoir. Compounds which may be used include almost any compound wih 2 oxygen functions such as ketones and esters. Mono keto or ester containing compounds such as mesityl oxide, pentanone-2 and methyl proportionate also show some stabilizing effect, but the amount required of such compounds to stabilize the methacryloxy containing organosilicon compounds toward polymerization will be much higher than those required fo diketones and ketoesters.

Diketones such as pentanedione-2,4 and hexadione-2,5 and ketoesters such as methyl acetoacetate are, therefore, the preferred comPounds to be used as stabilizer for the present invention or, more preferably, only the diketones.

The amount of stabilizer used may vary from 2 to 10 percent by weight based on the amount of metharcylate or acrylate used at the start, and more preferably from 2 to 5 percent.

EXAMPLES

The following specific examples and procedures are presented to illustrate the invention, but are not to be construed as limiting thereon.

| Definitions | |
|---|---|
| % | percent |
| g | gram or grams |
| hr | hour or hours |
| GC | gas chromotography |
| platinum | platinum |
| μl | microliters |
| ppm | parts per million |
| Insonox TM 129 | a phenolic stabilizer sold under this trademark name and generally available |
| PTZ | phenothizine |
| MMHQ | monomethyl ethers of hydroquinone |

EXAMPLE 1

Using a laboratory unit comprising two reservoirs, A and B, attached to a reaction vessel which was heated with an oil bath, a continuous preparation of γ-methacryloxypropyltrimethoxysilane was made as follows:

Before the peparation, the pump used for Reservoir A (allyl methacrylate) was preset to deliver toulene at a rate of about 2.5–3.0 g/minute and the oil bath heated to 110° C. Allyl methacrylate, 222 g, and Isonox TM 129, 2.22 g, were mixed and charged to reservoir A. When the temperature of the thermocouple reached about 95° C. (at a point where it measured the temperature of allyl methacryllate-Isonox TM 129 before the mixture met the reactants of the second reservoir), toluene delivery was stopped and the mixture of allyl methacrylate-Isonox TM 129 was pumped through to the reaction vessel. When most of the toluene in the unit was replaced by allyl methacrylate, trimethoxysilane, 108 g, was mixed with about 15 ppm of platinum catalyst, $H_2PtClphd$ 6, and charged to the unit via Reservoir B. The rate of trimethoxysilane pumped was adjusted first based on the predetermined allyl methacrylate rate to ensure that there was a 3 to 5molar excess of the methacrylate. It was further adjusted when gas chromatographic analysis of the first fraction of product collected showed too much or not enough trimethoxysilane. The objective of the adjustment was to obtain a crude γ-methacryloxypropyltrimethoxysilane mixture containing no or very little unreacted trimethoxysilane and about 3 to 5molar excess allyl methacrylate. The preparation was continued for about 5 hours and 1087 g of crude γ-methacryloxypropyltrimethoxysilane, identified by gas chromotography were collected. At the end of the preparation, toluene was again pumped through to wash the system free of the organosilane to preserve the unit for the next preparation.

The crude products collected were combined and stabilized with 1000 ppm of phenothiazine and 500 ppm of monomethylether of hydroquinone. The yield of γ-methacryloxypropyltrimethoxysilane calculated based on distillation data was 83.9% based on G.C. analysis.

EXAMPLES 2–6

The procedure used for Example 1 was repeated five more times. Variations in residence time, reaction temperature, crude product collected and yield of γ-methacryloxypropyltrimethoxysilane are summarized in Table 1.

TABLE I
CONTINUOUS PREPARATION OF γ-METHACRYLOXYPROPYLTRIMETHOXYSILANE

| No. | Residence Time (minutes) | Reaction Temp. (°C.) | Crude Product Collected Time (hr) | Crude Product Collected Weight (g) | Yield % (based on GC) |
|---|---|---|---|---|---|
| 2 | 24–28 | 100–106 | 5.7 | 1261 | 85.1 |
| 3 | 24 | 102–108 | 2.7 | 556 | 71.2 |
| 4 | 20.5 | 105–109 | 4.8 | 1037 | 83.5 |
| 5 | 17.7 | 105–108 | 4.0 | 1272 | 85.5 |
| 6 | 18.2 | 105–108 | 3.4 | 1217 | 85.3 |

EXAMPLES 7–13; COMPARATIVE EXAMPLES A AND B

The crude products collected from each experiment were divided and post treated with methanol and/or 120° C. heating for half an hour prior to distillation. They were then distilled to show the effect of post treatment. Results obtained are summarized in Table II.

TABLE II
EFFECT OF POST TREATMENT

| No. | Obtained from Experiment | Post Treatment 120° C. Heating | Post Treatment MeOH | Yield % (based on distillation product) |
|---|---|---|---|---|
| 7 | Exp. 2, Table I | Yes | Yes | 82.7 |
| 8 | Exp. 2, Table I | Yes | No | 81.1 |
| Comparative A | Exp. 2, Table I | No | No | Gelled |
| 9 | Exp. 2, Table I | No | Yes | 82.8 |
| 10 | Exp. 3, Table I | Yes | No | 69.3 |
| Comparative B | Exp. 3, Table I | No | No | 42.7 |
| 11 | Exp. 3, Table I | No | Yes | 70.3 |
| 12 | Exp. 4, Table I | No | Yes | 86.0 |
| 13 | Exp. 5, Table I | No | Yes | 80.9 |

From the above data, it can be seen that to obtain a uniform distillation stability, the crude product should be post treated with either heat or alcohol prior to distillation.

EXAMPLE 14

The same procedure of Example 1 was followed except that pentanedione- 2,4, 3.4 percent by weight, based on allyl methacrylate, was added to the mixture of allyl methacrylate and Isonox TM 129. The preparation was carried out for 3.1 hours and 977 g of crude product was collected. The yield of γ-methacryloxypropyltrimethoxysilane of the reaction based on GC data was 85.3%.

EXAMPLE 15

The same procedure of Example 1 was followed except that pentanedione-2,4, 3.4 percent by weight, based on allyl metharcylate, was added to the mixture of allyl methacrylate-Isononox TM 129 before it was charged into the unit and the platinum-catalyst used was dichlorobis(acetonitrile)-platinum (II). The preparation was carried out for 3.3 hours and 1036 g of crude product were collected during the period. Yield of reaction based on GC analysis was 83.4%.

EXAMPLE 16

The same procedure of Example 1 was followed except that the amount of allyl methacrylate was reduced to an allyl methacrylate/trimethoxysilane mole ratio of 0.98 and that pentanedione-2,4, 3.4 percent by weight, based on ally methacrylate-Isonox TM 129. The preparation was carried out for 3.5 hours . During the first 1.7 hours, about 15 ppm $Cl_2Pt(CH_3CN)_2$ was used as the platinum catalyst. For the next 1.8 hours, the platinum catalyst was switched to about 15 ppm $H_2PtCl_6$. Reaction temperature of the oil bath was 109°–113° C. The crude product, 555 g, was collected for the first 1.7 hours and 570 g for the next 1.8 hours. GC analysis of the crude products collected using the two platinum catalysts indicated the presence of 3.99 and 2.84 area % of unreacted trimethoxysilane, respectively. Yield of the reaction for the first half preparation was 84.8% and the second half, 84.5% based on G.C. analysis and based on the distillation product produced.

EXAMPLES 17-20

The crude products obtained from Examples 14, 15 and 16 were vacuum distilled in the presence of 1000 ppm of PTZ and 4000 ppm of MMHQ without the post treatment. Results obtained are listed in Table III.

TABLE III
VACUUM DISTILLATION OF
γ-METHACRYLOXYPROPYLTRIMETHOXYSILANE

| No. | Crude Product Made from | (MeO)$_3$SiH Left In Crude (Area %) | Yield % |
|---|---|---|---|
| 17 | 14 | 0.75 | 86.9 |
| 18 | 15 | 1.53 | 79.5 |
| 19 | 16 (1st Half) | 3.99 | 80.5 |
| 20 | 17 (2nd Half) | 2.84 | 84.7 |

From the above examples, it can be seen that γ-methacryloxypropyltrimethoxysilane made in the presence of pentanedione 2,4 is more stable than those made in the absence of pentanedione 2,4. As a result, the crude product made in the presence of pentanedione 2,4 not only can be made with stoichiometric amounts of allyl methacrylate, it can also be distilled without post treatment prior to distillation, even when 2-4% molar excess trimethoxysilane is present.

EXAMPLE 21 AND COMPARATIVE EXAMPLE C

The procedure of Example 1 was followed except that the trimethoxysilane pumping rate was adjusted in such a way that the first two fractions of crude γ-methacryloxypropyltrimethoxysilane contained 7-9% molar excess of unreacted trimethoxysilane and that the remaining fractions collected contained little or trace amounts of unreacted trimethoxysilane. The fractions were allowed to stand overnight at room temperature in the presence of 1000 ppm PTZ and 500 ppm MMHQ, based on the weight of product used. Both fractions which contained 7-9% excess unreacted trimethoxysilane (Comparative Example C) gelled overnight, while those fractions which had only little or trace amounts of trimethoxysilane (Example 21) remained as nonviscous liquid. These results indicate the effect of unreacted trimethoxysilane in the stability of crude γ-methacryloxypropyl-trimethoxysilane.

EXAMPLE 22

Into a 1000 ml four-necked round bottom flask, fitted with a mechanical stirrer, an addition funnel, a thermometer and a condenser were added Isonox TM 129, 2.6 g, and allyl methacrylate, 259 g, after the flask was flushed with dry air. To the addition funnel was added trimethoxysilane, 244 g. The reaction mixture was heated to 85° C., trimethoxysilane was dropped in and H$_2$PtCl$_6$ solution was added:

| (MeO)$_3$SiH | H$_2$PtCl$_6$ Solution | |
|---|---|---|
| After ¼ of total added | 180 μl | |
| ½ | 180 μl | — total = 650 μl |
| ¾ | 160 μl | (20 ppm platinum) |
| End of (MeO)$_3$SiH addition | 130 μl | |

During the addition, the mixture was kept at 85°-95° C. with cold water bath or heating. Heating was stopped when GC of the reaction mixture showed that all of the trimethoxysilane added had reacted.

PTZ, 1000 ppm, and MMHQ, 500 ppm, were added to the reaction mixture and the mixture was heated to 120° C. and kept at that temperature for one-half hour. The experiment was repeated for another five times; none of them showed any instability problems. Yield % of γ-methacryloxypropyltrimethoxysilane all remained in the range of 81-84% based on G.C. analysis.

EXAMPLE 23

The procedure used for Example 22 was followed except that the reaction was carried out on a scale of 1 mole trimethoxysilane and that the platinum catalyst was mixed with trimethoxysilane and dropped into allyl methacrylate Isonox TM 129 at 90°-100° C. Yield of γ-methacryloxypropyltrimethoxysilane calculated based on GC analysis was 81.3%.

COMPARATIVE EXAMPLE D

The procedure of Example 22 was followed except that 112.6 g of allyl methacrylate, 1.12 g of Isonox TM 129, 108 g of trimethoxysilane and 220 μl of a H$_2$PtCl$_6$ solution (platinum=15 ppm) were used and that the platinum catalyst was mixed with the allyl methacrylate Isonox TM 129 mixture and heated to 90° C. before trimethoxysilane was dropped in.

The experiment was repeated five times. Of the five experiments, three of them gelled when approximately 80-85% of the required trimethoxysilane was added to the reaction mixture. Yield of the other two experiments which did not gel was 66-68% according to GC analysis of the reaction mixture.

Comparison of Examples 22 and Comparative Example D indicates the importance of the method of platinum catalyst addition. The platinum catalyst should be reacted with the alkoxysilane prior to its addition to the methacrylate/inhibitor mixture to significantly reduce the chances of gelling.

EXAMPLE 24

The procedure of Comparative Example D was followed except that pentanedione 2,4, 3.8 g, was added to the allyl methacrylate Isonox TM 129-platinum catalyst mixture before the mixture was heated to 90° C. The experiment was repeated three times but none of them gelled during the hydrosilation. Yield of γ-methacryloxypropyltrimethoxysilane was 65-77%. Furthermore, the three reaction mixtures were also vacuum distilled without the post treatment in the presence of 1000 ppm PTZ and 4000 ppm of MMHQ prior to distillation. Yield of γ-methacryloxypropyltrimethoxysilane base on distillation data was 63-74based on G.C. analysis.

Therefore, the addition of pentaneione 2,4 to the reaction mixture has reatly reduced the ellation tendency of the γ-methacryloxypropyltrimethoxysilane so that the compound can be made even under those conditions which facilitate the gellation of the said compound, i.e., when the platinum catalyst is added before the silane or when no alcohol or post treatment step is used.

EXAMPLES 25-29; COMPARATIVE EXAMPLES E-K

To test the stability effect of various compounds, a series of experiments was carried out as follows:

Into a 50 ml three necked round bottom flask, fitted with a condenser, a thermometer and dry air inlet outlet tubing, were added 10 g of distilled γ-methacryloxypropyltrimethoxysilane, 0.0174 g of PTZ, 1.0 or 3.4 g of trimethoxysilane and the desired amount of the tested compound. The mixture was heated to 85° C. and platinum catalyst was added. Heating was continued and the temperature of the reaction mixture was kept at 95°-100° C. The time when change of viscosity of the reaction mixture was observed was recorded. Results obtained are summarized in Table IV.

It can be seen from the data that diketones are the most effective compounds to stabilize γ-methacryloxypropyltrimethoxysilane against polymerization in the presence of trimethoxysilane and platinum catalyst, or under conditions used for the preparation of methacryloxy-containing organosilicon compounds. Compounds containing keto and/or ester groups also show various degrees of stabilizing effect (for example, compare Comparative Examples E and F versus Examples 28 and 29 and Comparative Examples H-K), but the amounts required for these compounds to prevent the polymerization of methacryloxy-containing organosilicon compounds such as γ-methacryloxypropyltrimethoxysilane are much larger than those required when diketone such as pentanedione- 2,4 is used.

TABLE IV

EFFECT OF VARIOUS COMPOUNDS ON THE STABILITY OF q-METHACRYLOXYPROPYLTRIMETHOXYSILANE

| No. | (MeO)$_3$SiH Wt. % | Pt-Catalyst (Pt = 15 ppm) | Compound Tested (Wt. % Used) | Time when Change of Viscosity Observed |
|---|---|---|---|---|
| Comparative E | 34 | H$_2$PtCl$_6$ | None | Very viscous after 1 hour. |
| Comparative F | 34 | Cl$_2$Pt(CH$_3$CN)$_2$ | None | Very viscous after 1 hour. |
| 25 | 34 | Cl$_2$Pt(CH$_3$CN)$_2$ | Pentanedione-2,4 (7.8) | No visible change after 6-7 hrs. heating. |
| 26 | 34 | H$_2$PtCl$_6$ | Pentanedione-2,4 (7.8) | No visible change after 6-7 hrs. heating. |
| 27 | 10 | Cl$_2$Pt(CH$_3$CN)$_2$ | Pentanedione-2,4 (2.0) | No visible viscosity change after 6-7 hours heating. |
| Comparative G | 34 | Cl$_2$Pt(CH$_3$CN)$_2$ | Pentanedione-2,4 (2.0) | Noticeable viscosity change after 4-5 hours heating. |
| 28 | 34 | H$_2$PtCl$_6$ | Methyl acetoncetate (21.5) | No visible change after 6-7 hrs. heating. |
| Comparative H | 34 | H$_2$PtCl$_6$ | Methyl acetoncetate (10.7) | Visible viscosity change after 6 hrs. heating. |
| Comparative I | 34 | H$_2$PtCl$_6$ | Methyl proportionate (18.3) | Visible viscosity change after 6 hrs. heating. |
| Comparative J | 34 | H$_2$PtCl$_6$ | Pentanone-2 (16.2) | Visible viscosity change after 4 hrs. heating. |
| Comparative K | 34 | H$_2$PtCl$_6$ | Mesityl oxide (7.7) | Visible viscosity change after 1.5-2.0 hrs. |
| 29 | 10 | H$_2$PtCl$_6$ | Mesityl oxide (7.7) | No visible change after 6 hrs. heating. |

We claim:

1. A process for preparing methacryloxy or acryloxy containing organosilicon compounds without undesirable polymerization which process comprises:
   (a) charging a first reservoir with
     (i) 2-10% molar excess of a methacryloxy or acryloxy functional containing compound over a stochiometric amount of alkoxysilane or Si—H containing silicone which would be needed to form a complete reaction between said functional containing compound and said organosilane or silicone; and
     (ii) 0.2 to 5.0% of an inhibitor by weight based on the amount of methacryloxy or acryloxy used;
   (b) charging a second reservoir with
     (i) a stochiometric amount of alkoxysilane or Si—H containing silicone needed to form a complete reaction with the methacryloxy or acryloxy containing compound employed in (a); and
     (ii) a catalytic amount of platinum-containing hydrosilation catalyst;
   (c) combining the contents of the two reservoirs in a reactor vessel at 80°-120° centigrade.
   (d) post treating the crude reaction product with 1-5% alcohol by weight based on weight of product or post heating the reaction product for 5-40 minutes at 100°-140° C.; and
   (e) vacuum distilling the post-treated product in the presence of inhibitors and under reduced pressure.

2. A process for preparing methacryloxy or acryloxy containing organosilicon compounds without undesirable polymerization which process comprises:
   (a) charging a first reservoir with
     (i) 2 to 10% molar excess of a methacryloxy or acryloxy functional containing compound over a stochiometric amount of alkoxysilane or Si—H containing silicone which would be needed to form a complete reaction between said functional containing compound and said organosilane or silicone;
     (ii) 0.2 to 5.0% of an inhibitor by weight based on the amount of methacryloxy or acryloxy used; and
     (iii) a stabilizer;
   (b) charging a second reservoir with
     (i) a stochiometric amount of alkoxysilane or Si—H containing silicone needed to form a complete reaction with the methacryloxy or acryloxy containing compound employed in (a); and
     (ii) a catalytic amount of platinum containing hydrosilation catalyst;
   (c) combining the contents of the two reservoirs in a reactor vessel at 80° to 120° centigrade; and
   (d) vacuum distilling the product in the presence of inhibitors and under reduced pressure.

3. The process of claim 1 wherein the alkoxysilane is represented by the general formula:

$$R'Si(OR)_{3-n}$$
$$|$$
$$H$$

wherein R and R' are lower alkyl moiety containing 1–20 carbon atoms and n is 0–1.

4. The process of claim 3 where the lower alkyl moiety contains 1–4 carbon atom.

5. The process of claim 1 wherein the Si—H containing silicone is a polysiloxane polymer with the general formula:

$$R_3SiO[R_2SiO]_x[RSiO]_ySiR_3$$
$$|$$
$$H$$

where R is a lower alkyl group having 1 to 8 carbons or an aryl group having 6 to 10 carbons, x ranges from 0 to 100 and y ranges from 1 to 30.

6. The process of claim 5 wherein R is methyl.

7. The process of claim 1 wherein the methacryloxy or acryloxy functional containing compound is represented by the general formula:

$$CH_2=CCOO(x)_mCH_2CH=CH_2$$
$$|$$
$$R^2$$

wherein $R^2$ is hydrogen, a lower alkyl group having 2 to 8 carbons or an aryl group having 6 to 10 carbons, X is $CH_2CH_2O$ or a $CH_2$ or a combination of the two groups, and m equals 0 to 10.

8. The process of claim 7 wherein m eguals 0 to 5.

9. The process of claim 1 wherein the inhibitor is selected from the group consisting of phenolic inhibitors, aromatic amines, aromatic sulfur compounds and combinations thereof.

10. The process of claim 9 wherein the phenolic inhibitor is monomethyl ether of hydroquinone, Isonox TM 129 or Ionol.

11. The process of claim 9 wherein the aromatic amine is diphenylenediamine.

12. The process of claim 9 wherein the aroma is sulfur compound is phenothiazine.

13. The process of claim 1 wherein an inhibitor is used in the post treatment step.

14. The process of claim 13 wherein the inhibitor is selected from the group consisting of phenolic inhibitors, aromatic amines, aromatic sulfur compounds and combinations thereof.

15. The process of claim 14 wherein the phenolic inhibitor is monomethyl ether of hydroquinone, Isonox TM 129 or Ionol.

16. The process of claim 14 wherein the aromatic amine is diphenylenediamine.

17. The process of claim 14 wherein the aromatic sulfur compound is phenothiazine.

18. The process of claim 1 wherein the platinum containing hydrosilation catalyst is selected from the group consisting of supported platinum catalysts and homogeneous soluble platinum complexes.

19. The process of claim 11 wherein the supported platinum catalyst is platinum on γ-alumina or charcoal.

20. The process of claim 18 wherein the homogenous soluble platinum complex is selected from the group consisting of chloroplatinic acid, bis-(ethylene platinous)chloride, dichlorobis(acetonitrile)platinum (II), cis-dichlorobis(triphenylphosphine) platinum (II) and tetrakis(tetraphenylphosphine)platinum (O).

21. The process of claim 20 wherein the soluble platinum complexes are used as solutions in solvents.

22. The process of claim 21 wherein the solvents are isopropanol, acetonitrile or 1,2 dimethoxyethane.

23. The process of claim 1 wherein the first reservoir is additionally charged with a stabilizer.

24. The process of claim 2 wherein the alkoxysilane is represented by the general formula:

$$R'Si(OR)_{3-n}$$
$$|$$
$$H$$

wherein R and R' are lower alkyl moiety containing 1–20 carbon atoms and n is 0–1.

25. The process of claim 24 where the lower alkyl moiety contains 1–4 carbon atom.

26. The process of claim 2 wherein the Si—H containing silicone is a polysiloxane polymer with the general formula:

$$R_3SiO[R_2SiO]_x[RSiO]_ySiR_3$$
$$|$$
$$H$$

where R is a lower alkyl group having 1 to 8 carbons or an aryl group having 6 to 10 carbons, x ranges from 0 to 100 and y ranges from 1 to 30.

27. The process of claim 26 where R is methyl.

28. The process of claim 2 wherein the methacryloxy or acryloxy functional containing compound is represented by the general formula:

$$CH_2=CCOO(x)_mCH_2CH=CH_2$$
$$|$$
$$R^2$$

wherein $R^2$ is hydrogen, a lower alkyl group having 2 to 8 carbons or an aryl group having 6 to 10 carbons, X is $CH_2CH_2O$ or a $CH_2$ or a combination of the two groups, and m equals 0 to 10.

29. The process of claim 28 wherein m equals 0 to 5.

30. The process of claim 2 wherein the inhibitor is selected from the group consisting of phenolic inhibitors, aromatic amines, aromatic sulfur compounds and combinations thereof.

31. The process of claim 30 wherein the phenolic inhibitor is monomethyl ether of hydroquinone, Isonox TM 129 or Ionol.

32. The process of claim 30 wherein the aromatic amine is diphenylenediamine.

33. The process of claim 30 wherein the aromatic sulfur compound is phenothiazine.

34. The process of claim 2 wherein a inhibitor is used in the post treatment step.

35. The process of claim 34 wherein the inhibitor is selected from the group consisting of phenolic inhibitors, aromatic amines, aromatic sulfur compounds and combinations thereof.

36. The process of claim 35 wherein the phenolic inhibitor is monomethyl of hydroquinone, Isonox TM 129 or Ionol.

37. The process of claim 35 wherein the aromatic amine is diphenylenediamine.

38. The process of claim 35 wherein the aromatic sulfur compound is phenothiazine.

39. The process of claim 2 wherein the platinum containing hydrosilation catalyst is selected from the group consisting of supported platinum catalysts and homogeneous soluble platinum complexes.

40. The process of claim 39 wherein the supported platinum catalyst is platinum on γ-alumina or charcoal.

41. The process of claim 39 wherein the homogeneous soluble platinum complex is selected from the group consisting of chloroplatinic acid, bis-(ethylene platinous)chloride, dichlorobis(acetonitrile)platinum (II), cis-dichlorobis(triphenylphosphine) platinum (II) and tetrakis(tetraphenylphosphine)platinum (O).

42. The process of claim 41 wherein the soluble platinum complexes are used as solution in solvents.

43. The process of claim 42 wherein the solvents are isopropanol, acetonitrile or 1,2 dimethoxyethane.

44. The process of claim 2 wherein the stabilizer is selected from the group consisting of diketones and ketoesters.

45. The process of claim 44 wherein the diketone is pentadione- 2,4 or hexadione- 2,5.

46. The process of claim 44 wherein the ketoester is methyl acetoacetate.

47. The process of claim 44 wherein the stabilizer is additionally a mono keto or ester containing compound.

48. The process of claim 47 wherein the mono keto or ester containing compound is mesityl oxide, pentanone-2 or methyl proprionate.

49. A process for preparing methacryloxy or acryloxy containing organosilicon compounds without undesirable polymerization which process comprises:
(a) charging a first reservoir with
(i) 2–10% molar excess of a methacryloxy or acryloxy functional containing compound

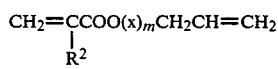

$$CH_2=CCOO(x)_mCH_2CH=CH_2$$
$$\phantom{CH_2=C}|$$
$$\phantom{CH_2=}R^2$$

wherein $R^2$ is hydrogen, a lower alkyl group having 2 to 8 carbons or an aryl group having 6 to 10 carbons, X is $CH_2CH_2O$ or a $CH^2$ or a combination of the two groups, and m is egual to 0 to 10 which excess is over a stochiometric amount of alkoxysilane or Si—H containing silicone which would be needed to form a complete reaction between said functional containing compound and said organosilane or silicone; and
(ii) 0.2 to 5.0% monomethyl ether of hydroquinone, Isonox ™ 129 or Ionol by weight based on the amount of methacryloxy or acryloxy used;
(b) charging a second reservoir with
(i) a stochiometric amount of an alkoxysilane

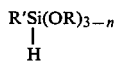

$$R'Si(OR)_{3-n}$$
$$|$$
$$H$$

where R and R' are lower alkyl moiety containing 1 to 20 carbon atoms and n is 0 to 1 or a stochiometric amount of an Si—H containing silicone

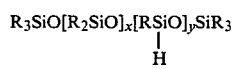

$$R_3SiO[R_2SiO]_x[RSiO]_ySiR_3$$
$$|$$
$$H$$

where R is a lower alkyl group having 1 to 8 carbons or an aryl group having 6 to 10 carbons, x ranges from 0 to 100 and y ranges from 1 to 30 which alkoxysilane or Si—H containing silicone is needed to form a complete reaction with the methacryloxy or acryloxy containing compound employed in (a); and
(ii) a catalytic amount of platinum-containing hydrosilation catalyst selected from the group consisting of supported platinum catalysts and soluble platinum complexes;
(c) combining the contents of the two reservoirs in a reactor vessel at 80°–120° centigrade;
(d) post treating the crude reaction product with 1–5% alcohol by weight based on weight of product or post heating the reaction product for 5–40 minutes at 100°–140° C.; and
(e) vacuum distilling the post treated product in the presence of phenolic or nonphenolic inhibitors under reduced pressure.

50. A process for preparing methacryloxy or acryloxy containing organosilicon compounds without undesirable polymerization which process comprises:
(a) charging a first reservoir with
(i) 2–10% molar excess of a methacryloxy or acryloxy functional containing compound

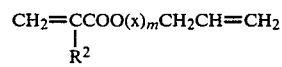

$$CH_2=CCOO(x)_mCH_2CH=CH_2$$
$$\phantom{CH_2=C}|$$
$$\phantom{CH_2=}R^2$$

wherein $R^2$ is hydrogen, a lower alkyl group having 2 to 8 carbons or an aryl group having 6 to 10 carbons, X is $CH_2CH_2O$ or a $CH_2$ or a combination of the two groups, and m is egual to 0 to 10 which excess is over a stochiometric amount of alkoxysilane or Si—H containing silicone which would be needed to form a complete reaction between said functional containing compound and said organosilane or silicone;
(ii) 0.2 to 5.0% monomethyl ether of hydroquinone, Isonox 129 or Ionol by weight based on the amount of methacryloxy or acryloxy used; and
(iii) stabilizer;
(b) charging a second reservoir with
(i) a stochiometric amount of an alkoxysilane

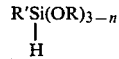

$$R'Si(OR)_{3-n}$$
$$|$$
$$H$$

wherein R and R' are lower alkyl moiety containing 1 to 20 carbon atoms and n is 0 to 1 or a stochiometric amount of Si—H containing silicone

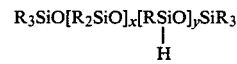

$$R_3SiO[R_2SiO]_x[RSiO]_ySiR_3$$
$$|$$
$$H$$

where R is a lower alkyl group having 1 to 8 carbons or an aryl group having 6 to 10 carbons, x ranges from 0 to 100 and y ranges 1 to 30 which alkoxysilane or Si—H containing silicone is needed to form a complete reaction with the methacryloxy or acryloxy containing compound employed in (a); and
(ii) a catalytic amount of platinum-containing hydrosilation catalyst selected from the group consisting of supported platinum catalysts and soluble platinum complexes;
(c) combining the contents of the two reservoirs in a reactor vessel at 80°–120° centigrade; and
(d) vacuum distilling the product in the presence of phenolic or nonphenolic inhibitors under reduced pressure.

51. The process of claim 50 wherein the stabilizer is selected from the group consisting of diketones and ketoesters.

52. The process of claim 50 wherein the diketone is pentadione- 2,4 or hexadione-2,5.

53. The process of claim 50 wherein the ketoester is methyl acetoacetate.

54. The process of claim 51 wherein the stabilizer is additionally a mono keto or ester containing compound.

55. The process of claim 54 wherein the mono keto or ester containing compound is mesityl oxide, pentanone-2 or methyl proprionate.

56. A process for preparin methacryloxy or acryloxy containin organosilicon compounds without undesirable polymerization which process comprises:
(a) charging a first reservoir with
(i) 3–5% molar excess of a methacryloxy or acryloxy functional containing compound

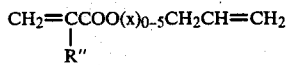

wherein R'' is hydrogen, a lower alkyl group having 2 to 8 carbons or an aryl group having 6 to 10 carbons, X is $CH_2CH_2O$ or a $CH_2$ or a combination of the two groups, over a stochiometric amount of alkoxysilane or Si—H containing silicone which would be needed to form a complete reaction between said functional containing compound and said organosilane or silicone; and
(ii) 0.5 to 2.0% monomethyl ether of hydroguinone, phenothiazine, or diphenylenediamine inhibitor by weight based on the amount of methacryloxy or acryloxy used;
(b) charging a second reservoir with
(i) a stochiometric amount of alkoxysilane

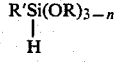

wherein R and R' are lower alkyl moiety containing 1 to 4 carbons and n is 0 to 1 or a stochiometric amount of an Si—H containing silicone

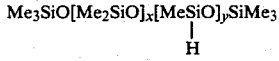

where x ranges from 0 to 100 and y ranges from 1 to 30 which alkoxysilane or Si—H containing silicone is needed to form a complete reaction with a given methacryloxy or acryloxy containing compound and
(ii) 2 to 20 parts per million of platinum on Y-alumina or charcoal;
(c) combining the contents of the two reservoirs in a reactor vessel at 80°–120° centigrade;
(d) post treating the crude reaction product with 1–3% alcohol by weight based on weight of product or post heating the reaction product for 20–30 minutes at 100°–140° C.; and
(e) vacuum distilling the post treated product in the presence of phenolic or nonphenolic inhibitors or diphenylenediamine and under reduced pressure.

57. A process for preparing methacryloxy or acryloxy containing organosilicon compounds without undesirable polymerization which process comprises:
(a) charging a first reservoir with
(i) 3–5% molar excess of a methacryloxy or acryloxy functional containing compound

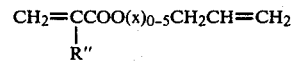

wherein R'' is hydrogen, a lower alkyl group having 2 to 8 carbons or an aryl group having 6 to 10 carbons, X is $CH_2CH_2O$ or $CH_2$ or a combination of the two groups, over a stochiometric amount of alkoxysilane or Si—H containing silicone which would be needed to form a complete reaction between said functional containing compound and said organosilane or silicone; and
(ii) 0.5 to 2.0% monomethyl ether of hydroquinone, Isonox ™ 129 or Ionol inhibitor by weight based on the amount of methacryloxy or acryloxy used;
(b) charging a second reservoir with
(i) a stochiometric amount of alkoxysilane

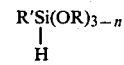

wherein R and R' are lower alkyl moiety containing 1 to 4 carbons and n is 0 to 1 or a stochiometric amount of an Si—H containing silicone

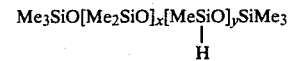

where x ranges from 0 to 100 and y ranges from 1 to 30 which alkoxysilane or Si—H containing silicone is needed to form a complete reaction with the methacryloxy or acryloxy containing compound employed in (a); and
(ii) 2 to 100 parts per million of homogeneous soluble platinum complex selected from the group consisting of chloroplatinic acid, bis-(ethyleneplatinous)chloride, dichlorobis(acetonitrile)-platinum (II), cis-dichlorobis(triphenylphosphine) platinum (II) and tetrakis(tetraphenyl phosphine)platinum (O);
(c) combining the contents of the two reservoirs in a reactor vessel at 90°–120° centigrade;
(d) post treating the crude reaction product with 1–3% alcohol by weight based on weight of product or post heating the reaction product for 20–30 minutes at 110°–130° C.; and
(e) vacuum distilling the post-treated product in the presence of phenolic or nonphenolic inhibitors under reduced pressure.

58. The process of claim 57 wherein the homogeneous soluble platinum complex is used as solution in solvents.

59. The process of claim 58 wherein the solvent is isopropanol, acetonitrile or 1,2 dimexhoxyethane.

60. A process for preparing, purifying and/or storing methacryloxy or acryloxy containing organosilicon compounds without undesirable polymerization which process comprises:
(a) charging a first reservoir with
(i) 3–5% molar excess of a methacryloxy or acryloxy functional containing compound

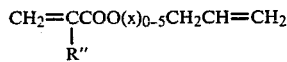

wherein R" is hydrogen, a lower alkyl group having 2 to 8 carbons or an aryl group having 6 to 10 carbons, X is $CH_2CH_2O$ or a $CH_2$ or a combination of the two groups, over a stochiometric amount of alkoxysilane or Si—H containing compound which would be needed to form a complete reaction between said functional containing compound and said organosilane or silicone; and
(ii) 0.5 to 2.0% monomethyl ether of hydroquinone, Isonox ™ 129, or Ionol inhibitor by weight based on the amount of methacryloxy or acryloxy used; and
(iii) stabilizer;
(b) charging a second reservoir with
(i) a stochiometric amount of alkoxysilane

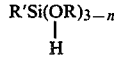

wherein R and R' are lower alkyl moiety containing 1–4 carbons and n is 0 to 1 or a stochiometric amount of an Si—H containing silicone

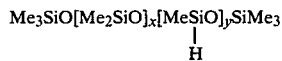

where x ranges from 0 to 100 and y ranges from 1 to 30 which alkoxysilane or Si—H containing silicone is needed to form a complete reaction with the methacryloxy or acryloxy containing compound employed in (a); and
(ii) 20–100 parts per million of platinum on Y-alumina or charcoal;
(c) combining the contents of the two reservoirs in a reactor vessel at 80–120° centigrade; and
(d) vacuum distilling the product in the presence of phenolic or nonphenolic inhibitors monomethyl ether of hydroquinone, phenothiazine or diphenylenediamine and under reduced pressure.

61. The process of claim 60 wherein the stabilizers is selected from the group consisting of diketones and ketoesters.

62. The process of claim 61 wherein the diketone is pentadione- 2,4 or hexadione 2,5.

63. The process of claim 61 wherein the ketoester is methyl acetoacetate.

64. The process of claim 61 wherein the stabilizer is additionally mono keto or ester containing compound.

65. The process of claim 64 wherein the mono keto or ester containing compound is mesityl oxide, pentanone-2 or methyl proprionate.

66. A process for preparing, purifying and/or storing methacryloxy or acryloxy containing organosilicon compounds without undesirable polymerization which process comprises:
(a) charging a first reservoir with
(i) 3–5% molar excess of a methacryloxy or acryloxy functional containing compound

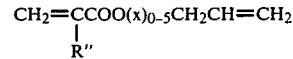

wherein R" is hydrogen, a lower alkyl group having 2 to 8 carbons or an aryl group having 6 to 10 carbons, X is $CH_2CH_2O$ or a $CH_2$ or a combination of the two groups, over a stochiometric amount of alkoxysilane or Si—H containing silicone which would be needed to form a complete reaction between said functional containing compound and said organosilane or silicone;
(ii) 0.5 to 2.0% monomethyl ether of hydroquinone, Isonox ™ 129 or Ionol inhibitor by weight based on the amount of methacryloxy or acryloxy used; and
(b) charging a second reservoir with
(i) a stochiometric amount of alkoxysilane

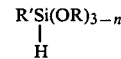

wherein R and R' are lower alkyl moiety 30 containing 1 to 4 carbons and n is 0 to 1 or a stochiometric amount of Si—H containing silicone

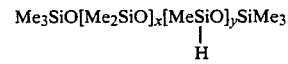

where x ranges from 0 to 100 and y ranges from 1 to 30 which alkoxysilane or Si—H containing silicone is needed to form a complete reaction with the methacryloxy or acryloxy containing compound employed in (a); and
(ii) 2 to 100 parts per million of homogeneous soluble platinum complex selected from the group consisting of chloroplatinic acid, bis-(ethyleneplatinous)chloride, dichlorobis(acetonitrile)platinum (II), cis-dichlorobis(triphenylphosphine) platinum (II) and tetrakis(tetraphenyl phosphine) platinum (O);
(c) combining the contents of the two reservoirs in a reactor vessel at 90°–120° centigrade; and
(d) vacuum distilling the product in the presence of phenolic and nonphenolic inhibitors and under reduced pressure.

67. The process of claim 66 wherein the stabilizer is selected from the group consisting of diketones and ketoesters.

68. The process of claim 67 wherein the diketone is pentadione- 2,4 or hexadione- 2,5.

69. The process of claim 67 wherein the ketoester ss methyl acetoacetate.

70. The process of claim 67 wherein the stabilizer is additionally a mono keto or ester containing compound.

71. The process of claim 70 wherein the mono keto or ester containing compound is mesityl oxide, pentanone-2 or methyl proprionate.

* * * * *